(12) United States Patent
Diehl (10) Patent No.: US 7,868,301 B2
(45) Date of Patent: Jan. 11, 2011

(54) DEFLECTING A BEAM OF ELECTRICALLY CHARGED PARTICLES ONTO A CURVED PARTICLE PATH

(75) Inventor: Dirk Diehl, Erlangen (DE)

(73) Assignee: Siemens Aktiengesellschaft (DE)

( * ) Notice: Subject to any disclaimer, the term of this patent is extended or adjusted under 35 U.S.C. 154(b) by 281 days.

(21) Appl. No.: 12/249,531

(22) Filed: Oct. 10, 2008

(65) Prior Publication Data

US 2009/0101832 A1 Apr. 23, 2009

(30) Foreign Application Priority Data

Oct. 17, 2007 (DE) .................. 10 2007 050 035

(51) Int. Cl.
*G01K 1/08* (2006.01)
*H01J 3/14* (2006.01)
*H01J 3/26* (2006.01)

(52) U.S. Cl. ................ 250/398; 250/396 ML; 250/492.1; 335/301; 335/210; 335/213; 335/214

(58) Field of Classification Search ........... 250/398, 250/396 ML, 492.1, 492.3; 335/301, 210, 335/213, 214
See application file for complete search history.

(56) References Cited

U.S. PATENT DOCUMENTS 6,677,597 B1 1/2004 Haberer et al.

2008/0315113 A1* 12/2008 Diehl et al. .............. 250/398
2009/0090871 A1* 4/2009 Diehl et al. .......... 250/396 R
2009/0091409 A1* 4/2009 Ries ....................... 335/213
2009/0321654 A1* 12/2009 Diehl et al. ........ 250/396 ML

FOREIGN PATENT DOCUMENTS

| DE | 199 07 771 A1 | 8/2000 |
|---|---|---|
| DE | 100 57 824 A1 | 6/2002 |
| DE | 10 2005 041 122 B3 | 5/2007 |
| EP | 1 045399 A1 | 10/2000 |

OTHER PUBLICATIONS

German Office Action dated Aug. 4, 2008 with English translation.

* cited by examiner

*Primary Examiner*—Jack I Berman
*Assistant Examiner*—Meenakshi S Sahu
(74) *Attorney, Agent, or Firm*—Brinks Hofer Gilson & Lione (57) ABSTRACT

A device for deflecting a beam of electrically charged particles onto a curved particle path is provided. The device includes at least one beam guidance magnet having a coil system which has at least one coil that is curved along the particle path for the purpose of deflecting the beam onto a curved particle path, and at least one scanner magnet for variably deflecting the beam in a y,z plane at right angles to the particle path, characterized in that the device has at least one correction system which is embodied to influence the particle path in a regulated or controlled manner with the aid of electric and/or magnetic fields as a function of the position of the beam in the y,z plane. The invention also relates to a corresponding method for deflecting a beam of electrically charged particles onto a curved particle path.

23 Claims, 8 Drawing Sheets

FIG 9   Exit sites and angles of the particles
(inclusion angle − 036.0072.036)

DEFLECTING A BEAM OF ELECTRICALLY CHARGED PARTICLES ONTO A CURVED PARTICLE PATH

This patent document claims the benefit of German patent application DE 10 2007 050 035.3, filed Oct. 17, 2007, which is hereby incorporated by reference.

BACKGROUND

The present embodiments relate to deflecting a beam of electrically charged particles onto a curved particle path.

Particle therapy includes accelerating ions of hydrogen (protons), carbon (C12) or other elements to high velocities (equivalent to energies of 50-500 MeV/nucleon) and directing the ions or other elements onto tumor tissue that is to be treated. The depth of penetration into the tissue can be set by varying the particle energy. The ions are generated and accelerated in a part of the system, which because of the part's size, that is stationary. The part of the system is immovable. The tumor may be irradiated from different directions. Accordingly, a movable magnet system for guiding and deflecting the ion beam may be provided. The magnet system may be adjustable in strength in order to enable an alignment with different particle energies, something which can be implemented effectively by electromagnets.

A magnet system that is able to rotate around the patient may be a gantry. A gantry comprises a system of magnets for deflecting and focusing ions of different energy and the mechanisms for mounting and rotating. The ion beam having a small beam diameter of a few millimeters exits the stationary generation and accelerator system and is injected into the gantry's magnet system, which is rotatable around the beam axis. In the gantry's magnet system, the beam experiences a deflection out of the rotational axis, focusing actions and further deflections before finally crossing the original beam axis in the isocenter at an obtuse angle, for example, at right angles to the rotational axis and hence to the original beam axis (compare FIG. 1). The deflections are implemented by dipole fields and the focusing actions by successive crossed quadrupole fields. To irradiate a spatially extensive tumor, the particle energy according to the depth of the tumor in the tissue may be varied and it's the energy along the two other spatial coordinates in the layer of this depth may be varied. Two scanner magnets, which are part of the gantry, can deflect the beam by a small angle in the horizontal and/or vertical plane since. In contrast to the other magnets, the scanner magnets can be driven very quickly. Adapting the current feed to the other deflection and focusing magnets in line with the respective particle energy can only be done slowly.

In one optical system, the scanner magnets are (other than shown in FIG. 1) the last ion-optic component of the gantry. The beam diameter can be kept small through the entire gantry, for example, the aperture and also the overall installation size of the previously traversed deflection and focusing magnets can be kept small. Due to the deflection caused by the scanner magnets, however, the particles strike the area to be treated at different angles. The particle beams may have a parallel incidence.

In another optical system, the scanner magnets are placed ahead of the terminating deflection magnet. Accordingly, the defocusing caused by the scanner magnets can be compensated by the following magnet, so the particles can exit the gantry in virtually parallel beams.

If magnets with iron yoke are used for the gantry, as is typically the case with ion-optic systems, the maximum magnetic flux density attainable is limited to about 2 Tesla due to saturation effects in the iron (or the ferromagnetic material used in this case). The achievable deflection radius is inversely proportional to the magnetic flux density. When ferromagnetic yoke material is used, the necessary deflection angle is only achieved with a size of magnet system that is unacceptable in terms of weight and costs. The use of superconducting air-core coils represents an alternative. Accordingly, considerably higher flux densities can be realized, with the result that the required deflection radius is reduced by the corresponding factor.

Figure 2:
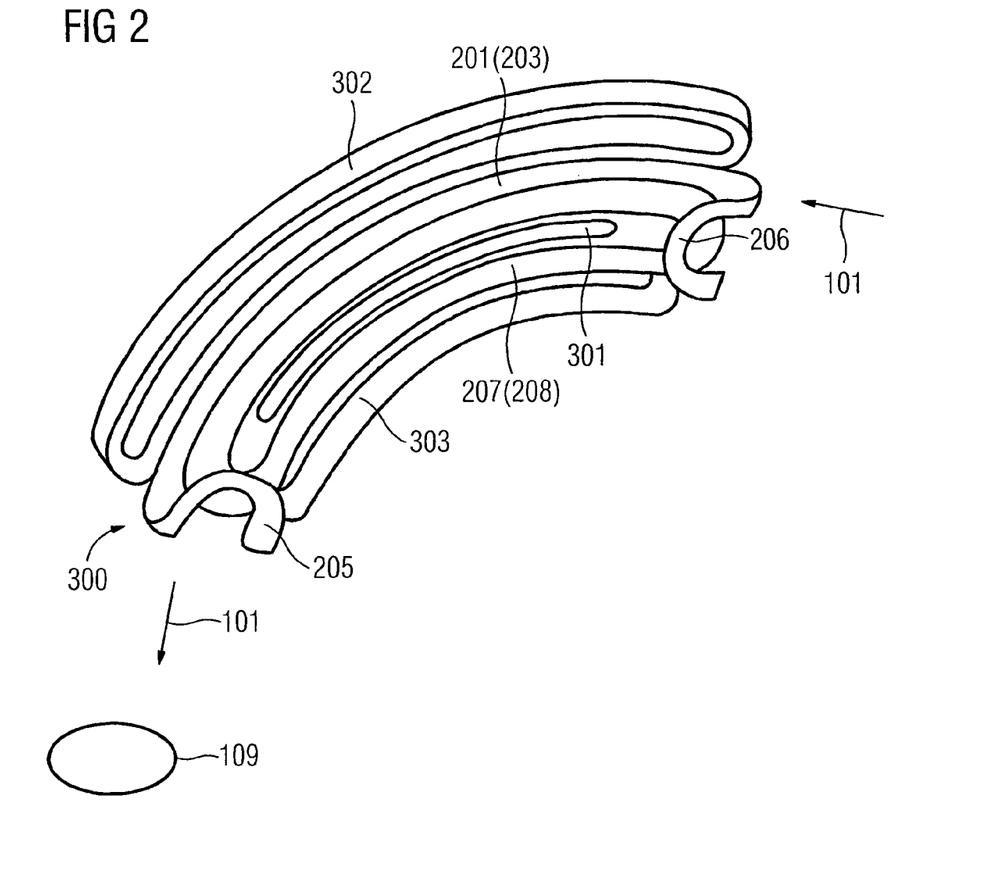
FIG. 2 illustrates a beam guidance magnet.

Only the final, terminating 90° deflection magnet is considered. The magnet can be implemented by individual coils with a rectangular cross-section, which enclose the volume of the particle beam. An actively shielded design includes, for example, two coils closed via the outsides and pairs of main, end and main correction coils are used, as shown in FIG. 2. The positions and cross-sections of the individual coils are usually chosen such that the ion-optic requirements for particle beams exiting in parallel and homogeneous spatial distribution of the particles are fulfilled.

Figure 3:
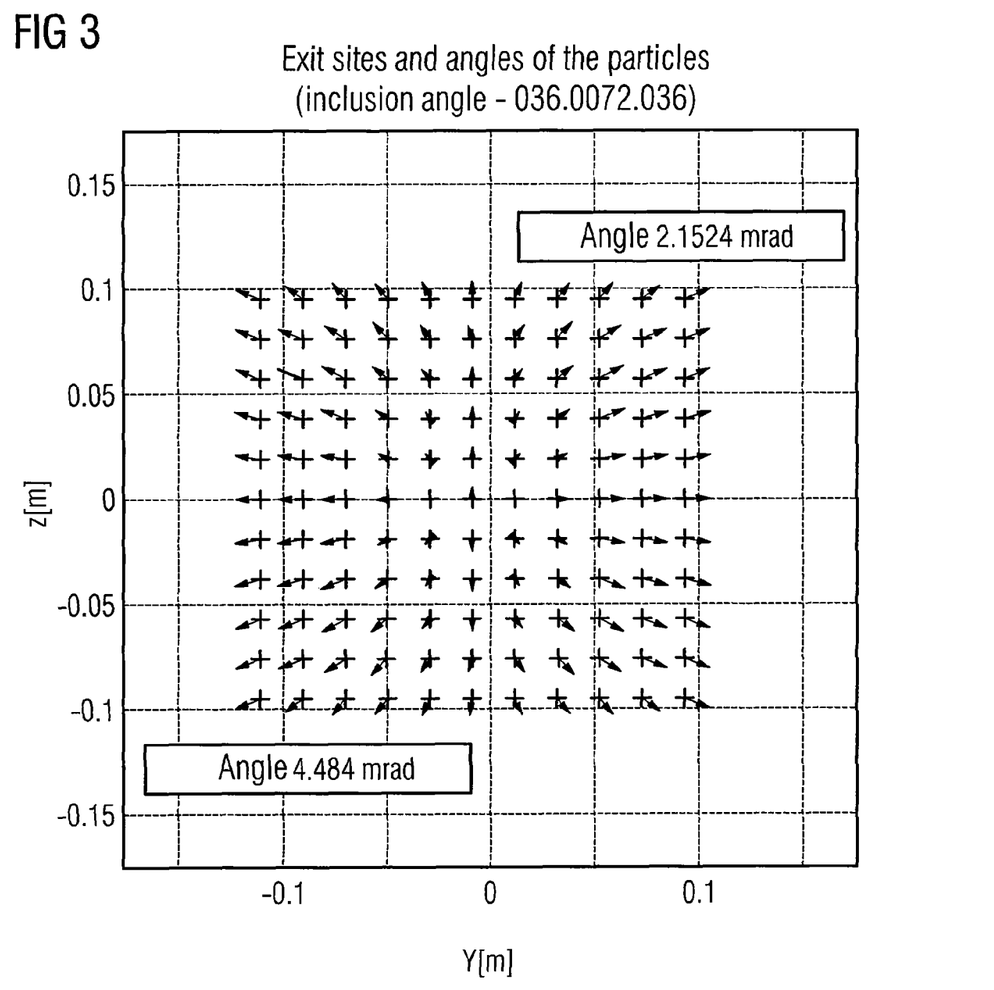
FIG. 3 illustrates exit sites and angular deviations in a plane of the isocenter at right angles to the main beam direction.

When a deflection magnet is being configured, a problem that routinely occurs is that the ion-optic requirements in terms of parallelism with at the same time homogeneous spatial distribution of the particles in the plane of the isocenter (for linearly driven scanner magnets) cannot be perfectly fulfilled in principle. FIG. 3 shows an example of a spatial and angular deviation for a coil configuration. When ferromagnetic components are used, for example, for shielding individual components, the B fields are no longer linear to the current, as a result of which the imaging can only be optimal for one ion energy.

The possibilities of fulfilling the ion-optic requirements (parallelism and desired spatial distribution) are essentially limited. Limitations arise, for example, from the limited current carrying capacity of real conductors. This also applies to superconductors, whose maximum current densities continue to be heavily dependent on the magnetic flux density at the location of the conductor.

Arbitrarily high requirements in terms of parallelism with simultaneous homogeneous spatial distribution can only be achieved with very great deflection radii. This, however, conflicts with the requirement for wanting to implement as compact and lightweight a deflection magnet as possible.

SUMMARY AND DESCRIPTION

The present embodiments may obviate one or more of the drawbacks or limitations inherent in the related art. For example, in one embodiment, a device deflects a beam of electrically charged particles onto a curved particle path. The device allows maximally precise beam guidance in a simple manner also in the case of a scanned particle beam.

In one embodiment, a device for deflecting a beam of electrically charged particles onto a curved particle path is provided. The device includes at least one beam guidance magnet and at least one scanner magnet. The at least one beam guidance magnet has a coil system which has at least one coil that is curved along the particle path for the purpose of deflecting the beam onto a curved particle path. The at least one scanner magnet variably deflects the beam in a y,z plane at right angles to the particle path, the device having at least one correction system which is embodied to influence the particle path in a regulated or controlled manner with the aid of electric and/or magnetic fields as a function of the position of the beam in the y,z plane.

In another embodiment, a method for deflecting a beam of electrically charged particles onto a curved particle path is provided. The method includes deflecting the beam onto a curved particle path using at least one beam guidance magnet having a coil system which has coils that are curved along the particle path, variably deflecting the beam in a y,z plane at right angles to the particle path using at least one scanner magnet having a coil system, and additionally deflecting the beam as a function of the position of the particle path in the y,z plane by regulating or controlling at least one correction system having a correction regulating or control unit and having a correction deflection unit.

In one embodiment, a correction system may be used to compensate for inaccuracies in the deflection of the beam by the deflection magnet, for example, as a function of the position of the beam in the plane at right angles to the particle path. The correction system controls or regulates the particle path differently according to the position of the beam in the y,z plane and corrects the position of the beam and/or the deviation in the direction of the beam, for example, from a main beam direction. The correction system may include at least one correction coil and/or at least one correction capacitor by which a magnetic or electric field is generated.

DETAILED DESCRIPTION

Figure 1:
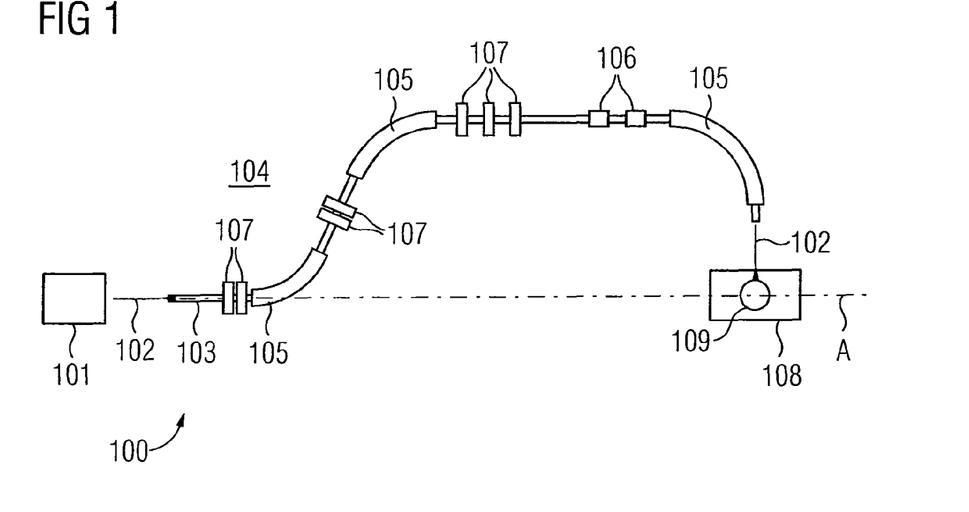
FIG. 1 illustrates an irradiation facility (system) including a gantry system.

FIG. 1 shows an irradiation facility 100 by which a beam of electrically charged particles (particle beam) 102 emerging from a particle source or accelerator 101 is deflected along a curved particle path with a gantry system. The particle beam 102 may be a beam of $C^{6+}$ ions. The particle beam 102 is guided inside a beam guidance tube 103. A beam guidance plane 104 is the curved path of the particle beam 102. The particle beam 102 is deflected (or, as the case may be, focused) several times from a direction predefined by the particle source or accelerator 101 from the particle beam's 102 original direction by a plurality of deflection magnets 105 and/or quadrupole magnets 107. Deflection magnets 105 and/or quadrupole magnets 107 and further magnets, for example, scanner magnets 106, are part of the gantry system which is rotatable around a specified rotation axis A. In addition to the deflection magnets 105, quadrupole magnets 107 and scanner magnets 106, a gantry system includes a frame for mounting the corresponding magnets.

The gantry system may direct the particle beam 102 into an isocenter 109. An isocenter 109 is an area in which the particle beam 102 intersects the gantry rotation axis A. During a rotation of the gantry system, the particle beam 102 runs consistently through the isocenter 109. The isocenter 109 is located inside an irradiation zone 108. If an irradiation facility 100 is used, for example, for cancer treatment, a tumor or phantom that is to be irradiated with $C^{6+}$ ions, for example, is located in the area of the isocenter 109.

FIG. 2 shows a beam guidance magnet in a side view. The beam guidance magnet may be a 90° deflection magnet. The beam guidance magnet may deflect the particle beam by 90°, for example. The beam guidance magnet may include a plurality of coil systems.

Figure 4:
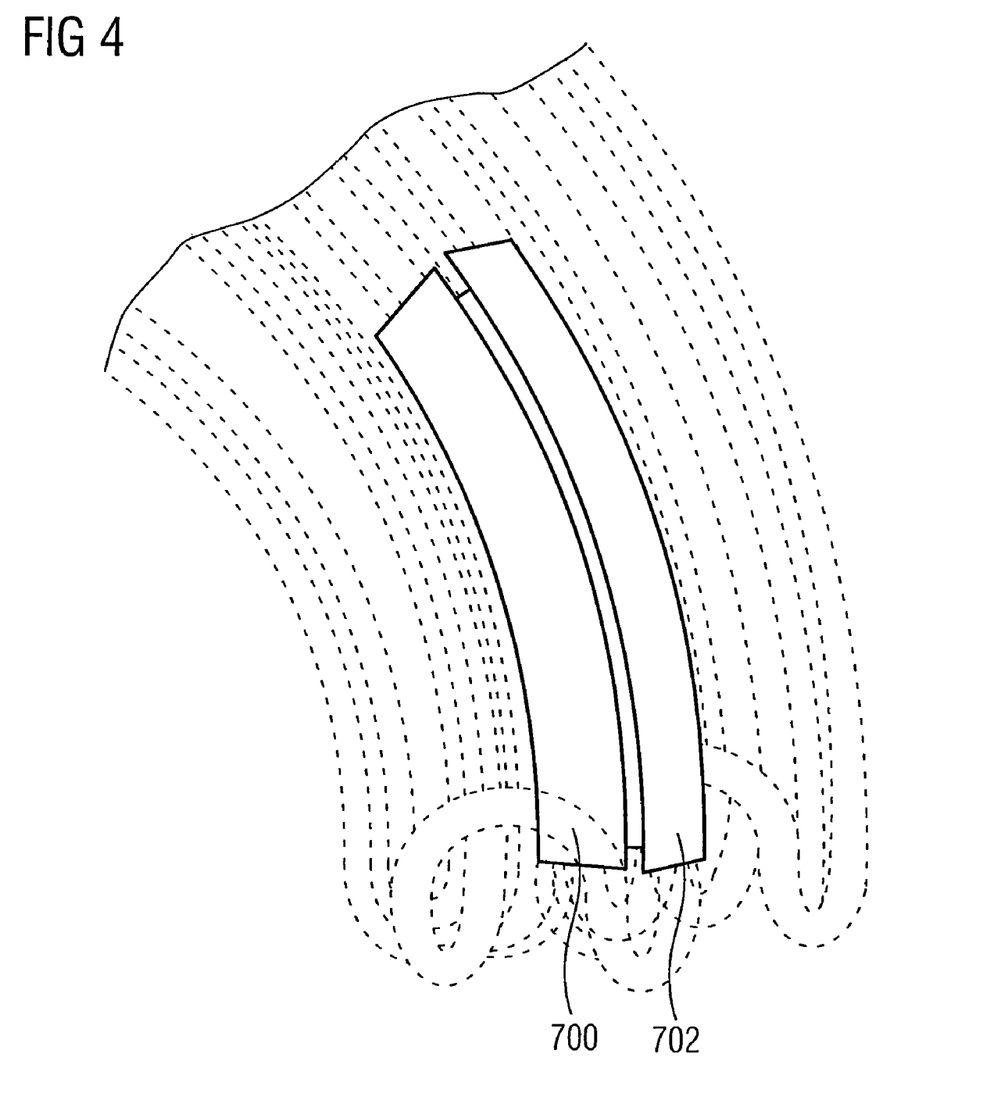
FIG. 4 illustrates a beam guidance magnet with two electrode pairs.

The coil system may include a first and second coil subsystem. FIG. 2 shows the individual coils of a first and second coil subsystem. The first coil subsystem comprises two main coils 201. FIG. 4 shows one of the two main coils. The corresponding second main coil, which is arranged laterally reversed with respect to the beam guidance plane, lies congruent with the first main coil. The first main coils 201 each have bent-up end parts 205, 206. The secondary coils 207 are located between the bent-up end parts 205, 206. The main coils 201 each have elongate side parts 203 along the particle path, while the secondary coils 207 each have largely flat, elongated side parts 208.

The end parts 205, 206 of the main coils 201, 202 may be bent upward in such a way that they overlap with the arcuate end parts 209, 210 of the secondary coils 207 in the projection into the beam guidance plane.

The second coil subsystem includes two second main coils 302, 303, which are each curved in a banana shape and are disposed in the area of the beam guidance plane between the first main coils 201. The two second main coils 302, 303 each have a section close to the particle path and a side part distant from the particle path.

The coil system may include main correction coils 301 arranged in the inner area of the secondary coil. A beam of electrically charged particles 101 may be deflected into an isocenter 109 by the coil system shown in FIG. 2.

FIG. 3 shows in the plane of the isocenter the exit sites (crosses) and angular deviations from an ideal vertical incident direction (arrows) when an uncorrected deflection magnet, as shown for example in FIG. 2, is used for deflecting the particle beam.

In one embodiment, the deflection magnet includes additional electrode pairs on the output side and inside the beam tube. The additional electrode pairs may be placed under voltage in pairs individually for the horizontal and vertical deflection independently of the current feed to the magnet system of the deflection magnet in order to allow small angular corrections by means of an electric field. The electrode pairs may be capacitors, such as parallel-plate capacitors.

Figure 5:
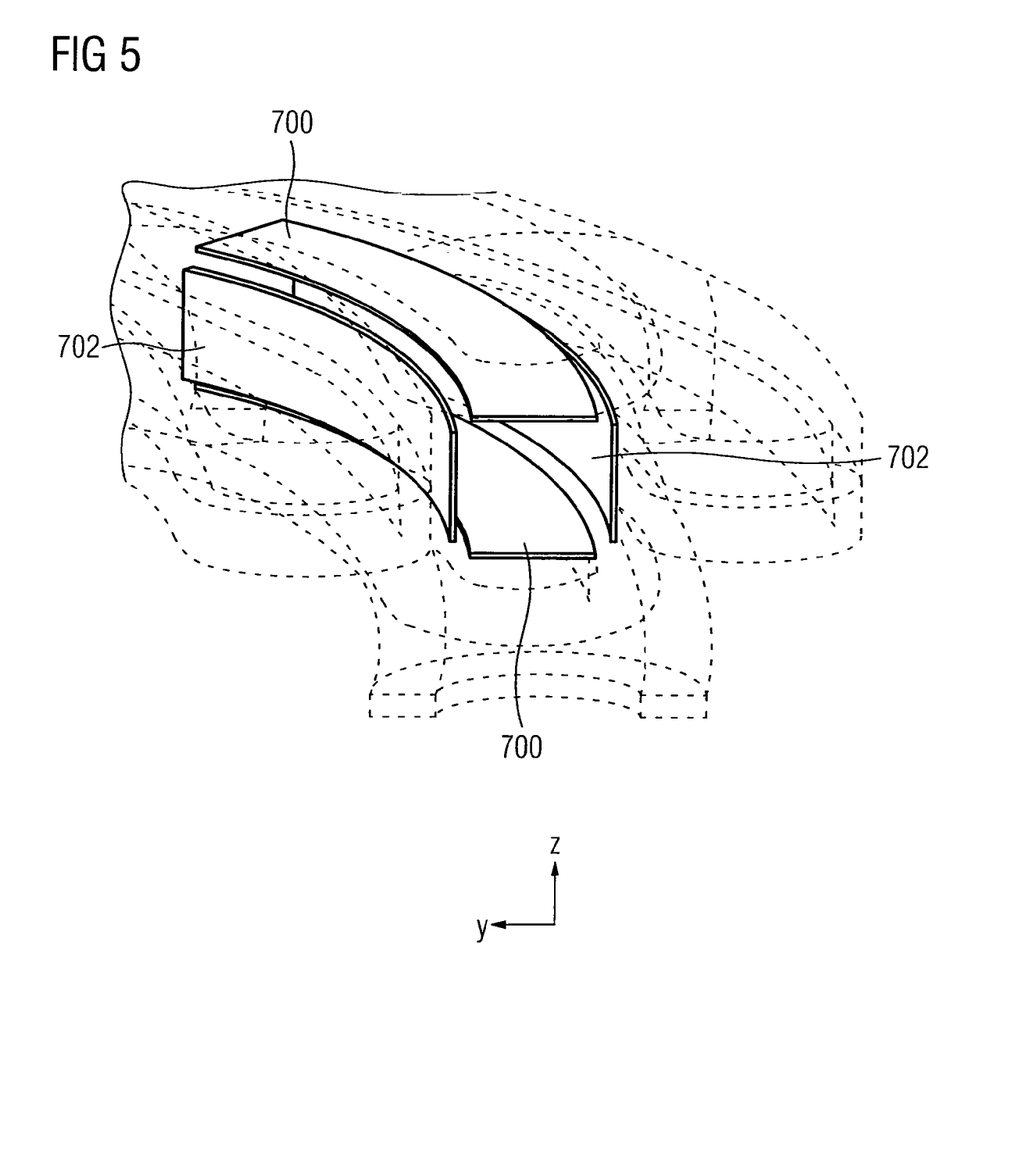
FIG. 5 illustrates a beam guidance magnet with two electrode pairs.

FIGS. 4 and 5 show electrode pairs 700, 702. The coils of the deflection magnet surrounding the electrode pairs 700, 702 are shown transparently in order to allow a view onto the electrode pair. A first electrode pair 700 enables the deflection of the particle beam in the y-direction (horizontal direction) while the second electrode pair 702 enables the deflection of the particle beam in the z-direction (vertical direction).

The two electrode pairs 700, 702 may be driven simultaneously and according to strength in accordance with the necessary correction for both directions for the respective beam. Initially an increased spatial deviation can be associated with this. However, this can likewise be fully compensated by appropriate control of the scanner magnets (angular correction during injection of typically less than 1 mrad).

The following numerical example is intended to illustrate the technical practicability of the driving of the electrode pairs:

For the angular correction of the deflection of a $C^{6+}$ ion at 430 MeV/u by 10 mrad—which is more than twice as large as is necessary for the distribution for correction purposes shown in FIG. 3—an electric field strength of approximately 200 kV/m along half the path length inside the magnet is necessary, for example, if the electrode pairs cover 45° on the inside of the beam tube, as shown in FIG. 4. At an electrode spacing of 0.2 m, a voltage of 40 kV has to be applied (see also FIGS. 5 and 6).

For lower-energy $C^{6+}$ ions, correspondingly weaker electric fields and lower voltages are required.

The energy change in the ions when speeding through the electric correction field is negligibly small, since the field strength-path length product is small and the direction of the electric field is almost vertical to the movement direction of the ions. The field strength-path length product is associated only with a change in direction but not a change in velocity of the ions.

The angular deviation for each beam, which for treatment purposes has only a small extension relative to the aperture of the magnet (e.g. 1 to 5 mm beam diameter relative to 200×200 $mm^2$ aperture), can be fully corrected for each location within the aperture by the electric field that is built up between the electrode pairs 700, 702. With the aid of the individually driven electrode pairs in conjunction with the appropriate control of the scanner magnets it is possible to cause a beam of small extension to exit precisely at each location within the aperture exactly in parallel and correct the unavoidable imaging errors of the magnet system.

The magnet system of the main magnet should already have satisfactory imaging characteristics, as shown in FIG. 3. Remaining inaccuracies may be corrected. Greater deviations, for example, distortions of the beam spot (a beam with round cross-section could exit the deflection magnet with a slightly elliptical cross-section for example) cannot be corrected by the above device and method. The requirements in terms of the ion-optic characteristics with regard to the beam distortions are relatively minor compared to angular and spatial deviations. The correction method and the device are suitable for magnet arrangements that include nonlinear materials such as ferromagnetic shields, which essentially cannot have optimal imaging characteristics for all ion energies simultaneously.

Figure 9:
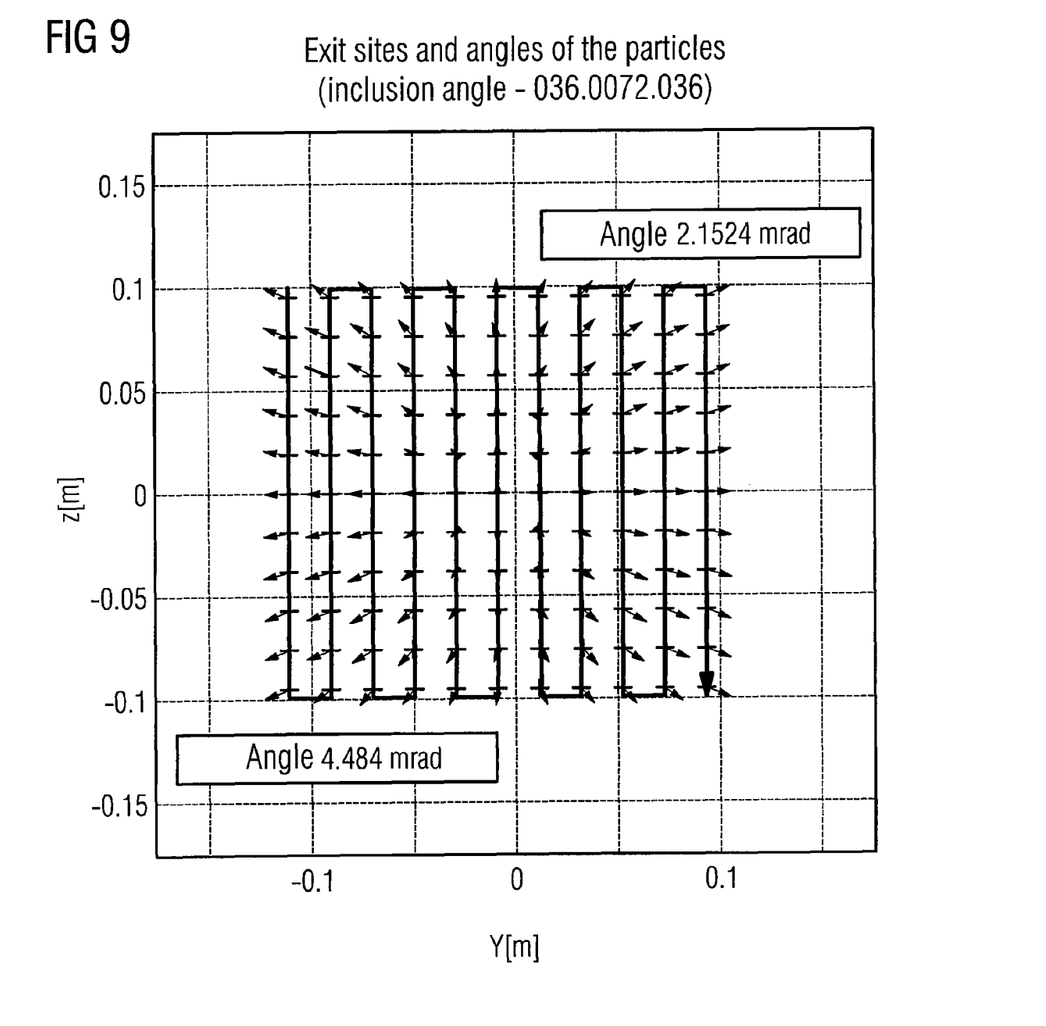
FIG. 9 is a diagram according to FIG. 3 in which the scan curve in the plane of the isocenter is drawn.

To reduce the absolute value of the maximum drive voltage for correction in the horizontal direction, the current feed to the magnet system and the scanner control for each scan row (as indicated in FIG. 9) may be set such that the positive and negative angular deviations are of equal size in terms of absolute value. The drive voltages for each row are minimized symmetrically around zero and the absolute value of the voltage is reduced to a minimum.

A corresponding correction for the vertical direction is usually not necessary as long as the magnet system is mirror-symmetrical to the z=0 plane, since for reasons of symmetry the angular deviation are then also symmetrical.

The absolute value of the electrode voltage and the risk of a flashover are reduced. The use of an electric field for small angular corrections has the advantage that correction may be performed quickly, since only small capacitances have to be recharged, which permits the voxel-by-voxel or pixel-by-pixel correction during the scanning. There is no coupling of the magnet system to a correction apparatus that is based on electric fields, in contrast to such an apparatus that is based on magnetic fields (i.e. a correction coil system).

Figure 6:
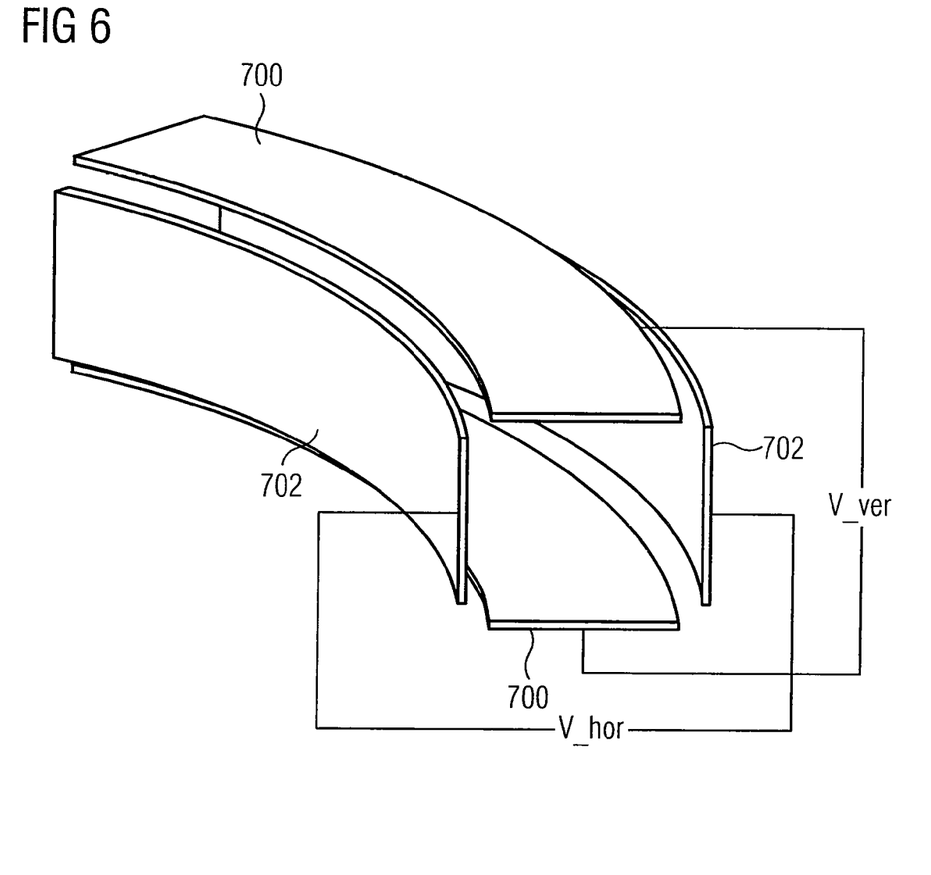
FIG. 6 illustrates electrode pairs with control voltages for horizontal and vertical deflection.

FIG. 6 shows the driving of the electrode pairs 700, 702 by control voltage for the horizontal and vertical deflection, respectively.

In one embodiment, the deflection magnet includes additional correction coil pairs (for example, at the output of the magnet), which can be driven in pairs individually for the horizontal and vertical deflection independently of the current feed to the main magnets. Accordingly, a spatial deviation may be initially increased. The increased spatial deviation may be compensated by suitable control of the scanner magnets (angular correction during injection of typically less than 1 mrad).

Figure 7:
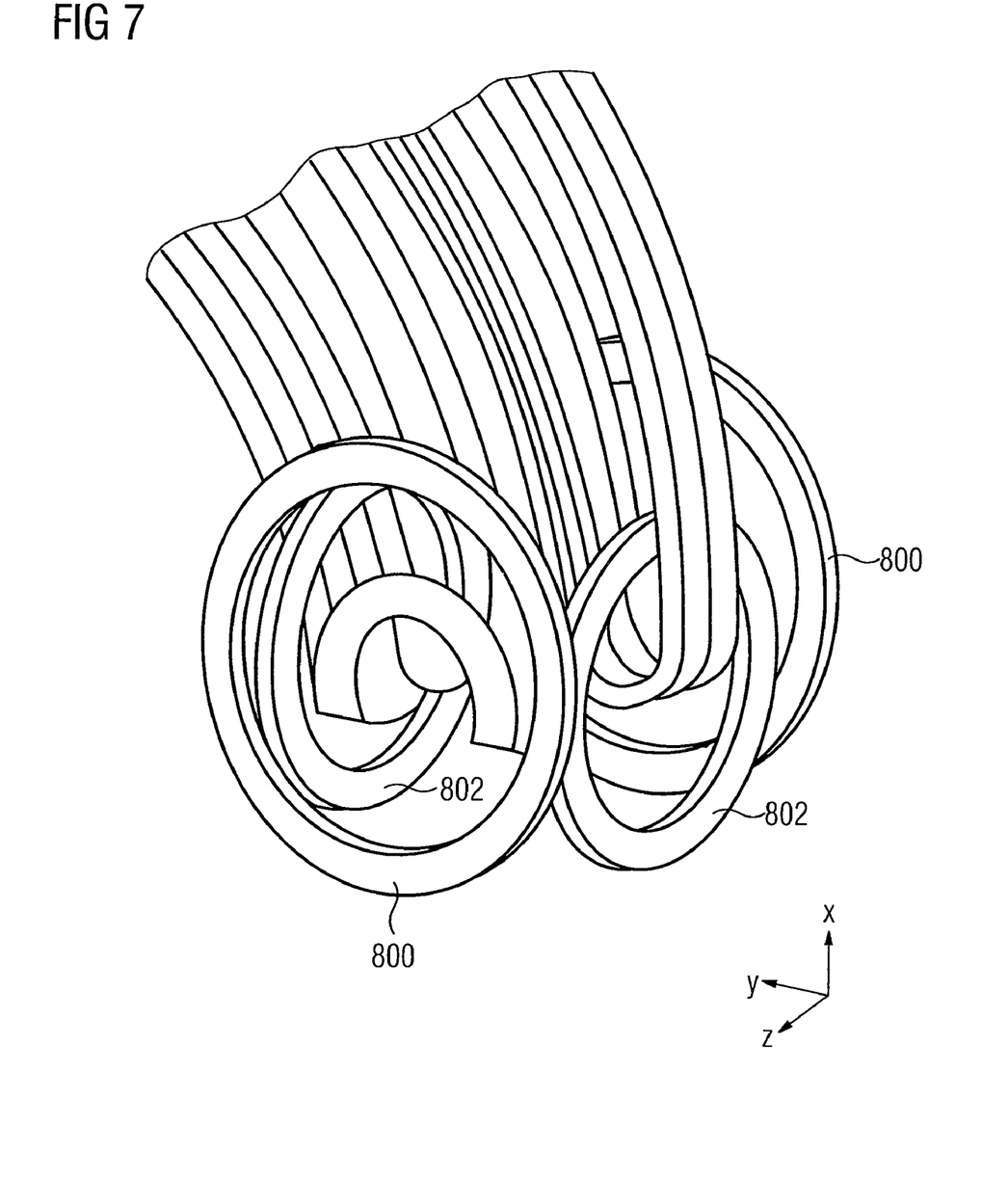
FIG. 7 illustrates a beam guidance magnet with two correction coil pairs.
Figure 8:
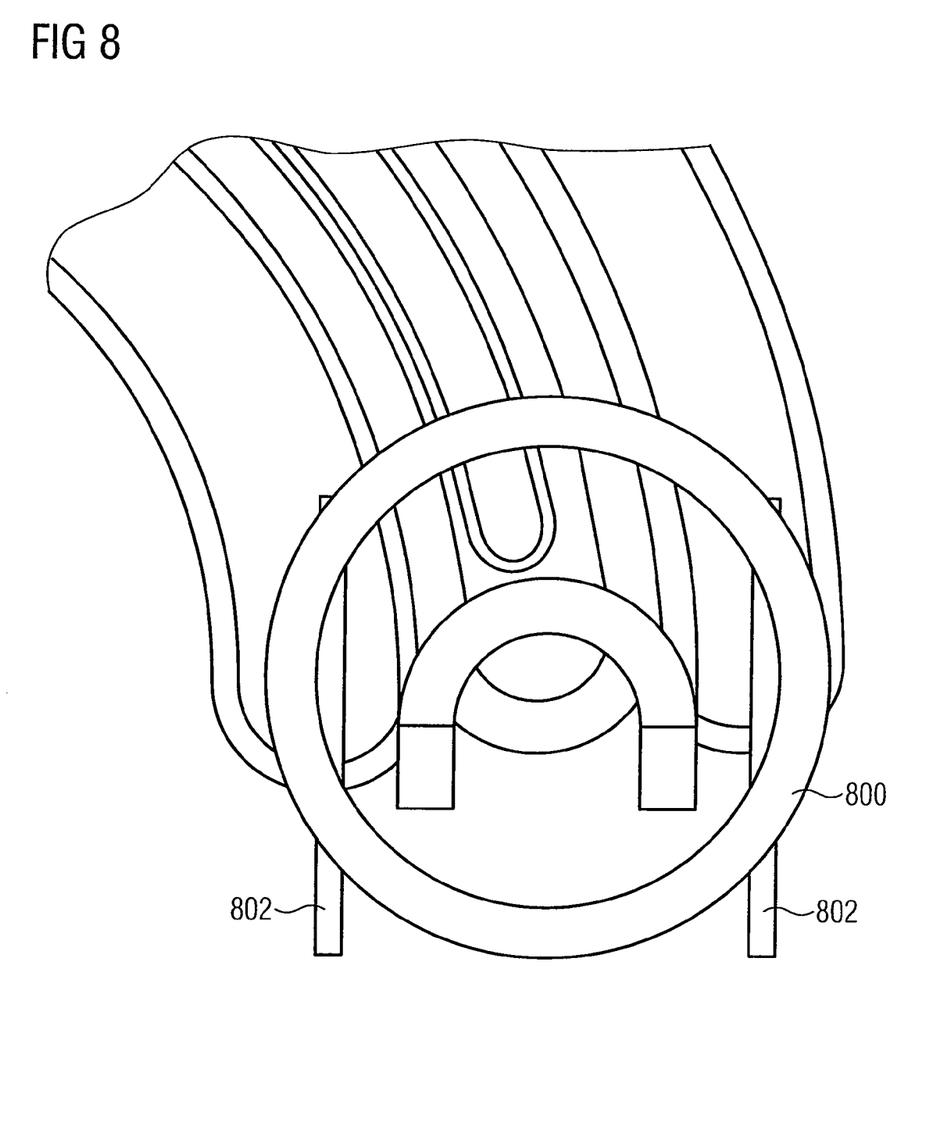
FIG. 8 illustrates a beam guidance magnet in a side view with two correction coil pairs.

FIGS. 7 and 8 show correction coil pairs. FIG. 7 shows a first correction coil pair 800 for the deflection in the y-direction (horizontal direction) and a second correction coil pair 802 arranged at right angles thereto for the deflection in the z-direction (vertical direction).

The correction coils 800, 802 may suppress the angular deviation for each beam, which for treatment purposes has only a small extension relative to the aperture of the magnet (e.g. 1 to 5 mm beam diameter relative to 200×200 $mm^2$ aperture), for each location within the aperture. The individually driven correction coil pairs 800, 802 and suitable control of the scanner magnets may cause a beam of small extension to exit precisely at each location within the aperture exactly in parallel and correct the unavoidable imaging errors of the main magnet.

The magnet system of the main magnet may have satisfactory imaging characteristics, as shown in FIG. 3. The remaining inaccuracies may be corrected all the more easily. Greater deviations, for example, distortions of the beam spot (a beam with round cross-section could exit the deflection magnet with a slightly elliptical cross-section for example) cannot be corrected by the above device and method. However, the requirements in terms of the ion-optic characteristics with regard to the beam distortions are relatively minor compared to angular and spatial deviations. The correction method and the device are suitable for use in particular for magnet arrangements that include nonlinear materials such as ferromagnetic shields which essentially cannot have optimal imaging characteristics for all ion energies simultaneously.

In one embodiment, the first correction coil pair 800 for horizontal deflection may be omitted and the current feed to the main magnet is corrected. This saves on a correction coil pair 800 and its current source.

The high inductance of the main magnet may make it difficult to effect quick current changes due to the high voltages and the AC losses occurring in the superconductor (e.g., when a superconducting magnet is used). In one embodiment, the current feed to the main magnet may be set to the mean value of the correction current for a scan row (compare FIG. 9) and the correction performed from voxel to voxel by the horizontal first correction coil pair 800.

Only one current change (relative current change in the order of magnitude of less than 1 per mill) is necessary per row for the main magnet and the mean value of the correction current across a row disappears in the first correction coil pair 800, as a result of which lower losses into the, for example, normally conducting correction coil occur.

The correction coil pairs 800, 802 may include a strong inductive coupling of the correction coils and the coils of the main magnet. Quick current changes in the correction coils can then induce high voltages in the main coil system, which can then be corrected by the main coil system's current source.

The high voltages may be counteracted by incorporating the drive signals for the current feed to the correction coils in accordance with the coupling to the main coil system as a correction variable into the regulation or control of the current source of the main coil system. Alternatively, an additional controlled voltage source can equally be connected in series with the main coil system and the main coil current source, which voltage source compensates the induction voltage due to the correction coil current change in accordance with the control. The current regulation in the main coil system may be improved or made easier.

The following numerical examples are intended to underline the technical practicability of the control of the correction coils.

For the angular correction of the deflection of a $C^{6+}$ ion at 430 MeV/u by 10 mrad (which is more than twice as large as for the distribution shown in FIG. 3) a flux density of approximately 90 mT is required in the center of the first correction coil pair 800, where the coils have a 1 m spacing and 0.5 m radius. This flux density is achieved for a magnetomotive force per coil of approximately 100 kA*turns. Each individual correction coil of the pair for horizontal deflection with a radius of 0.5 m and cross-section of 5×10 $cm^2$ has an inductance of approximately 1.6 µH for one turn. If the magnetomotive force is distributed over 500 turns (conductor current 200 A; the coil cross-section can possibly be increased in order to reduce the current density), this results in an individual coil inductance of 0.4H. If 100 voxels 2 mm in size are radiated along a row 200 mm every 1 s, one row lasts 100 s. If a frequency of 1/100 s is derived from this for the change from −10 . . . 10 mrad, then a voltage of only 10 V needs to be applied to the series-connected correction coil pair, which technically is easily possible. (For comparison: gradient amplifiers for use in MRI applications deliver voltages up to 2 kV at currents up to 500 A and rise times of 200 µs.)

Correspondingly smaller flux densities and currents are required for lower-energy carbon ions.

Whether the correction coil pairs 800, 802 are normally conducting or superconducting can be assessed on the basis of the different loss contributions and the cooling concept of the overall magnet arrangement. Both are possible from the ion-optic viewpoint.

FIG. 9 shows the curve of a scanned particle beam along a y,z plane which is scanned in rows arranged in the y-direction.

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. A device for deflecting a beam of electrically charged particles onto a curved particle path, the device comprising:
   at least one beam guidance magnet having a coil system that has at least one coil curved along the particle path for deflecting the beam onto a curved particle path,
   at least one scanner magnet that variably deflects the beam in a y,z plane at right angles to the particle path, and
   at least one correction system that regulates or controls the particle path using electric and/or magnetic fields as a function of the position of the beam in the y,z plane.

2. The device as claimed in claim 1, wherein the correction system is operable to correct a deviation of the particle path from a reference value in the y,z plane and/or to correct a deviation of the particle path from a beam direction parallel to a main beam direction.

3. The device as claimed in claim 1, wherein the correction system comprises a correction regulating or control unit that generates a regulating or control signal and a correction deflection unit that is operable to change the particle path as a function of the regulating or control signal.

4. The device as claimed in claim 1, wherein the correction deflection unit includes at least one electrode pair in the form of a parallel-plate capacitor.

5. The device as claimed in claim 4, wherein the correction deflection unit comprises a first parallel-plate capacitor that is operable to generate a first deflection of the beam in a first direction in the y,z plane, and a second parallel-plate capacitor that is operable to generate a further deflection of the beam in a direction at right angles to the first direction in the y,z plane.

6. The device as claimed in claim 1, wherein the correction deflection unit includes at least one correction coil.

7. The device as claimed in claim 6, wherein at least two correction coils are arranged oppositely in pairs in the correction deflection unit.

8. The device as claimed in claim 7, wherein the correction deflection unit comprises a first pair of correction coils, which are operable to generate a deflection of the beam in a first direction in the y,z plane, and a second pair of correction coils which are operable to generate a further deflection of the beam in a direction at right angles to the first direction in the y,z plane.

9. The device as claimed in claim 1, wherein the correction system is controlled by correction current and/or correction voltage, the correction current and/or correction voltage being independent of a control current of the at least one beam guidance magnet.

10. The device as claimed in claim 1, wherein the at least one scanner magnet is arranged along the movement direction of the particles upstream of the at least one beam guidance magnet.

11. The device as claimed in claim 1, wherein the at least one correction deflection unit is disposed in an area of the beam exit of the at least one beam guidance magnet.

12. The device as claimed in claim 1, further comprising a rotatable gantry.

13. The device as claimed in claim 12, wherein the correction deflection unit is inside a beam tube of the rotatable gantry.

14. A method for deflecting a beam of electrically charged particles onto a curved particle path, the method comprising:
   deflecting the beam onto a curved particle path using at least one beam guidance magnet having a coil system which has coils that are curved along the particle path,
   variably deflecting the beam in a y,z plane at right angles to the particle path using at least one scanner magnet having a coil system, and
   an additional deflection of the beam is effected as a function of the position of the particle path in the y,z plane by regulating or controlling at least one correction system as a function of the position of the particle path in the y,z plan using an additional deflection of the beam,
   wherein the at least one correction system includes a correction regulating unit or control unit and a correction deflection unit.

15. The method as claimed in claim 14, wherein the correction regulating or control unit regulates or controls capacitors and/or correction coils which are disposed in the correction deflection unit.

16. The method as claimed in claim 15, wherein the correction deflection unit is regulated or controlled via current and/or voltage.

17. The method as claimed in claim 16, wherein correction coils are driven in pairs individually or jointly and/or correction capacitors are driven individually or jointly for a y deflection and/or z deflection in the y,z plane.

18. The method as claimed in claim 14, wherein the correction deflection unit is controlled independently of the control of the beam guidance magnets.

19. The method as claimed in claim 14, wherein the correction deflection unit is controlled for a deflection direction in the y,z plane, and the at least one beam guidance magnet regulates or controls the correction of the deflection in a deflection direction at right angles to the deflection direction in the y,z plane.

20. The method as claimed in claim 14, wherein the control of the scanner magnets compensates for the deviation of the points of intersection of the particle path with the y,z plane from desired reference positions, brought about by the correction deflection unit.

21. The method as claimed in claim 14, wherein a current of the at least one beam guidance magnet is set to a mean value of a correction current required for a scan row, and the correction is effected by controlling or regulating the correction deflection unit as a function of the position of the particle path in the y,z plane.

22. The method as claimed in claim 14, wherein the beam guidance magnet is controlled or regulated as a function of the interaction between correction deflection unit and beam guidance magnet and of the control or regulation of the correction deflection unit.

23. The method as claimed in claim 14, wherein the beam guidance magnet is controlled via an additional controlled voltage source as a function of the control or regulation of the correction deflection unit.

* * * * *